United States Patent
Lehman

(10) Patent No.: US 8,561,618 B2
(45) Date of Patent: Oct. 22, 2013

(54) ADJUSTABLE NASAL PASSAGE EXPANDER

(76) Inventor: Andrew Lehman, Scottsdale, AZ (US)

(*) Notice: Subject to any disclaimer, the term of this patent is extended or adjusted under 35 U.S.C. 154(b) by 335 days.

(21) Appl. No.: 12/927,503

(22) Filed: Nov. 16, 2010

(65) Prior Publication Data
US 2011/0152921 A1 Jun. 23, 2011

Related U.S. Application Data

(60) Provisional application No. 61/284,604, filed on Dec. 18, 2009.

(51) Int. Cl.
*A61F 5/56* (2006.01)
*A61F 5/08* (2006.01)

(52) U.S. Cl.
USPC .. 128/848; 128/200.24; 606/199; 606/204.45

(58) Field of Classification Search
USPC .................. 606/199, 204.45; 128/848, 858, 128/206.23–206.25, 200.24
See application file for complete search history.

(56) References Cited

U.S. PATENT DOCUMENTS

| | | | | |
|---|---|---|---|---|
| 5,284,469 A | * | 2/1994 | Jasen et al. | 602/17 |
| 6,029,658 A | * | 2/2000 | De Voss | 128/200.24 |
| 6,065,470 A | * | 5/2000 | Van Cromvoirt et al. | 128/200.24 |
| 6,375,667 B1 | * | 4/2002 | Ruch | 606/199 |
| 6,860,263 B1 | | 3/2005 | Scoggins | |
| 7,456,332 B2 | | 11/2008 | Beaudry | |
| 2001/0023695 A1 | | 9/2001 | Auriemma | |
| 2005/0161046 A1 | * | 7/2005 | Michaels | 128/206.14 |
| 2008/0097517 A1 | * | 4/2008 | Holmes et al. | 606/199 |
| 2009/0183734 A1 | * | 7/2009 | Kwok et al. | 128/200.24 |

* cited by examiner

Primary Examiner — Patricia Bianco
Assistant Examiner — Kari Petrik
(74) Attorney, Agent, or Firm — Snell & Wilmer L.L.P.

(57) ABSTRACT

An article to improve nasal passage air flow may be a strip that comprises a flexible resilient material, and has a first end and a second end, and a top surface and a bottom surface, with at least a portion of the bottom surface at the first end of the strip comprising a first adhesive surface, and at least a portion of the bottom surface at the second end of said strip comprising a second adhesive surface. The strip may serve to dilate a user's nasal passage when the first end of the strip is secured using the first adhesive bottom surface to be proximate to an alar facial groove of the user's nose, with the second end of the strip being pulled up at a slight angle and laterally to achieve desired nasal passage expansion and thereafter being secured to the user's face, at roughly a 20-25 degree angle.

6 Claims, 11 Drawing Sheets

ADJUSTABLE NASAL PASSAGE EXPANDER

CROSS REFERENCES TO RELATED APPLICATIONS

This application claims priority on U.S. Provisional Application Ser. No. 61/284,604 filed on Dec. 18, 2009, the disclosures of which are incorporated herein by reference.

FIELD OF THE INVENTION

The present invention is directed to articles for improving the flow of air through a person's nasal passages, and more particularly, to articles which may be applied to a person's face to assist in opening nasal passages.

BACKGROUND OF THE INVENTION

Presently in the market there is a nasal strip that is positioned over the nose and sold under the trademark Breathe Right. These strips claim to open the nasal passageways to reduce snoring and relieve congestion. The strip is comprised of a plastic substrate, woven material, and adhesive that is adhered by the user around the bridge of the nose. The nasal expansion occurs due to the plastic substrates memory wanting to straighten out versus being bent around the bridge of the nose. The adhesive holds the device in place which results in pulling up the nostril and achieving expansion of the air passage way.

United States Published Patent No. 2001/0023695 to Auriemma discloses a rectangular shaped nasal dilator. This dilator is applied to the cheek area of a user away from the nose and is claimed to prevent the nasal passage of the nose from constricting during breathing. There is an adhesive layer on either end of the substrate. The strip is positioned proximate the cheek bone of the user with a first area of adhesive at one end of the strip. The strip extends rearwardly towards the ear of the user where the adhesive on the second end is affixed to the skin of the user between the cheek bone and the ear on the face of the user. At paragraph 0024 of the published application Auriemma states that the nasal dilator is positioned on the face beneath the eye adjacent to the nose and proximate the zygomatic bone (cheek bone). The dilator is then drawn rearwardly toward the ear whereupon the second end of the dilator is affixed to the skin so that the dilation is "affixed to the facial portion of the individual proximate the nose, beneath the eye and above the zygomatic or cheek bone and extends circumferentially rearwardly in the direction A towards the ear." The Auriemma strip is a rectangular strip with generally square adhesive areas on one side thereof. The square adhesive regions are separated by a rectangular adhesive free region. The Auriemma strips are not positioned in proximity to the outside surface of the nose. In a second embodiment there is a flexible resilient strap which extends above the head of the individual.

U.S. Pat. No. 7,456,332 to Beaudry discloses a dressing and epidermal positioning mechanism. The strips generally have a rectangular center portion and at least one circular portion with adhesive thereon. The opposite side may have a circular adhesive portion or a trapezoidal portion. The articles are positioned over the nose like the Breathe Right strips.

Kwok, U.S. Published Patent Application No. 2009/0183734 shows a strip that is positioned away from the nose and not to the nose. FIG. 2 shows a rectangular strip that has two rectangular end portions that are secured to the face along the cheekbones and which extend toward the ear and are secured to the face just in front of the ear. In an alternative, the securing device could engage behind the wearer's ear like a pair of eyeglasses. Another patent that shows a nasal dilator that is secured around the head is shown in U.S. Pat. No. 6,860,263 to Scoggins.

While there are a number of different nasal dilators, in addition to the need for other products and variations, the Adjustable Nasal Passage Expander invention herein has distinct and measurable advantages in its design, function, and end results that improve air flow for users.

OBJECTS OF THE INVENTION

It is an object of the invention to provide a nasal passage expander that improves nasal airflow.

It is another object of the invention to provide a nasal passage expander that may be worn in proximity to the side of the nose that delivers enhanced results versus the version positioned across the nose or the version that is positioned beneath the eye.

It is also an object of the invention to provide nasal passage expanders that may be worn on the cheeks on opposite sides of the nose in multiple sizes, shapes and application positions designed to achieve increased nasal airflow.

It is a further object of the invention to provide a nasal passage expander that is adjustable and which gives the user the ability and flexibility to control the amount of expansion of the nasal passageways.

It is also an object of the invention to provide a nasal passage expander that extends from one edge of the nose to the side of the cheek bone that is the furthest away from the nose. It is a further object of the invention that the length and positioning increases the amount of nasal expansion, airflow and results for the user.

It is another object of the invention to provide a nasal expander that increases air flow during sleep, enhances energy and impact stamina and performance during sports activities and/or delivers relief from congestion resulting from allergies, a cold or similar conditions.

It is a further object of the invention that it has a sleep, cold and/or allergy version plus a sports version.

It is a further object of the invention that the sports version acts as an anti-glare feature while increasing nasal airflow to enhance endurance during sport related activities.

It is also an object of the invention to provide a nasal passage expander that may reduce or eliminate snoring in some users.

It is still a further object of the invention to provide an adjustable nasal passage expander that does not need to be secured by straps or arms that go over the ears or around the head.

It is still another object of the invention to provide a nasal passage expander that is decorative.

SUMMARY OF THE INVENTION

While there are a number of different nasal dilators available, the present invention incorporates unique characteristics of size, shape, positioning, methods of application, and adjustability, and furthermore achieves improved nasal airflow to satisfy the growing need for improved air flow for many users. The nasal passage expander of the present invention may include a strip of a flexible sheet material, which may comprise a woven or a non-woven substrate. The expander preferably has a length greater than its width. At one end of the strip there may be a concave arcuate portion that permits the strip to be positioned as close as possible to the outer surface of the nose in the area of the side of the nose adjacent the opening of the nostril. Generally this area of the nose is called the alar facial groove or junction which is adjacent the alar sidewall. On opposite sides of the concave arc there are first and second corner members. The corner members are preferable rounded ends extending outwardly of the strip.

Extending along the length of the strip is a first sidewall and a second sidewall. The first sidewall has a generally concave configuration. However, the portion of the sidewall adjacent the corner member adjacent the first sidewall preferably has a steeper descending run than the portion of the strip that extends inwardly of the opposite end. The second sidewall is generally convex in configuration over a portion of its length. The first sidewall and the second sidewall are not parallel to each other and connect to form a curved end, the second end, i.e., the end opposite the first end with the concave arc portion discussed above. The second sidewall has an area between the first portion which is adjacent the first end of the strip with the concave arc and the center portion of the sidewall. This first portion may be provided with a slight recess. There is a second portion of the sidewall that is from the area of the center of the sidewall to the second end of the strip. The second sidewall curves upward to the second end of the strip. The arrangement of the first and second sidewalls gives the strip a configuration where the second end is higher than the first end when the strip is on a user's face.

The outside surface of the strip may be any suitable color desired. The surface may be a single color or combination of colors. In another embodiment the strip may be provided with a design, including decorative features, a logo, insignia or other figures to enhance the visual attributes of the strip. In an alternative embodiment the strip may have one end positioned on the side of the cheekbone adjacent the side of the nose and the other end of the strip on the opposite side of the cheekbone. For sports enthusiasts the outer surface of the strip may be black or a non reflective color so that light reflecting off the cheeks does not bother the user's eyes.

The underside of the strip preferably has one or more adhesive areas. In one embodiment, the underside of the strip has a first adhesive bearing area adjacent the first end of the strip. There also is a second adhesive bearing area adjacent the second end of the strip. Between the two adhesive bearing areas there is preferably an adhesive free region. The adhesive areas on the strip can be adjusted, in terms of the type of adhesive used and the degree of its adherence to a skin surface, based on the desired use—i.e. sleep, allergy/cold relief, sports and cardio-vascular activity, etc. The shape of the adhesive surface may also be varied. The first adhesive bearing region is preferably bean shaped or shaped, i.e., having a first side that is the concave arc of the first end of the strip and an opposite side of the adhesive area having a generally convex or arcuate edge. One end of the adhesive conforms to the shape of the second end of the strip. The adhesive may be any suitable adhesive. Preferably, the adhesive utilized is a medical grade F.D.A. approved adhesive for skin contact, however other non FDA approved adhesives can be utilized as well. In certain applications an aggressive adhesive may be desirable that will not release during activities such as running, spinning, cardio, football, basketball, baseball, soccer, hockey, tennis, etc. While certain shapes have been described for the strip and the adhesive areas, it will be appreciated that there may be modifications to the shapes. The size of the strip can also vary depending on the size of the user's face and based on other variables.

The strip of the present invention may be positioned with the first end, i.e., the end or edge with the concave arc adjacent to the user's nose. This area is called the alar facial groove or junction and the strip has a curved shape at one end due to the shape of the alar. The concave shape permits the strip to be secured to the face as close to the outer surface of the nose as possible. The second end is positioned along the cheek of the wearer, wrapping around the cheekbone to achieve maximum results and increased nasal airflow. To apply the strip, it is preferable that the first end be secured as close to the outside of the nose (outer edge of the nostril) as possible. While pressure is applied to the end of the strip adjacent to the nose the strip is gently pulled out and up toward and around the cheek bone to expand the nasal passage to a desired length of nasal expansion and secure the second end on the outer end of the cheekbone is positioned on the face of the user thereby retaining the nasal passageways in a more open position. In a preferred embodiment the end of the strip opposite the alar is secured to the area of the face on the distal side of the cheekbone with respect to the nose. While the second end of the strip can be secured to the proximate side of the cheekbone i.e., the side of the cheekbone closest to the alar groove, a longer strip may be used so that it may be secured to the distal side of the cheekbone. In a preferred embodiment of the present invention, the strip may comprise a strip of sufficient length to at least go over/across the cheek bone to be secured thereto.

The present invention provides an increased air flow, so a user can breathe more freely during sleep. In addition, the strips enhance energy and impact performance during sport activities as well as deliver relief from congestion resulting from allergies or a cold or other similar conditions. Use of the strips also serves to reduce or eliminate snoring, to reduce the detrimental effects of sleep apnea, and also generally improves the rest, energy, and health of its users.

DETAILED DESCRIPTION OF THE INVENTION

Figure 1:
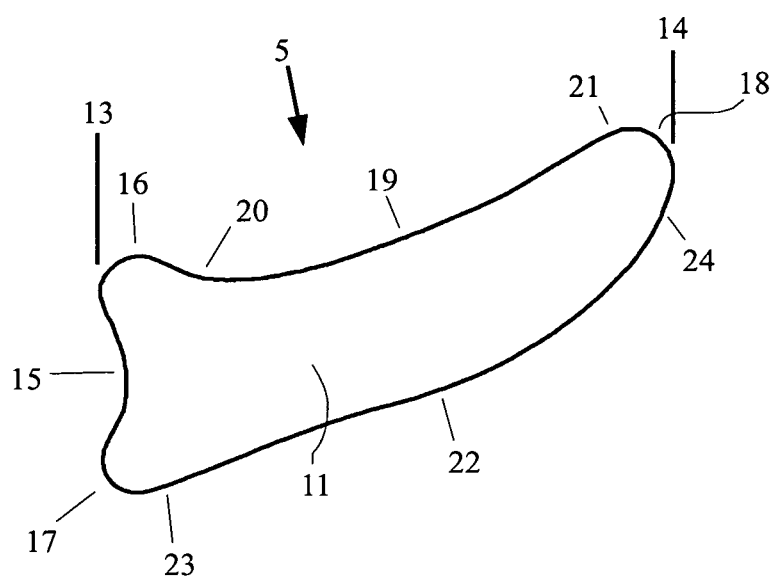
FIG. 1 is a top view of a nasal passage expander in accordance with the present invention.

The adjustable nasal passage expander or nasal dilator of the present invention may be a strip 5 that is made of a flexible material that is able to twist and generally conform to a contoured surface. The flexible strip material may be any suitable material, such as a thermoplastic film or sheet. The flexible strip may be a single layer, or may comprise multiple layers. The strip may also comprise a single layer throughout one portion of the strip, while comprising multiple layers throughout one or more other areas of the strip. One preferred material is polypropylene based sheet material or a Tricot sheet material. Other suitable materials include polyolefins, polyesters, etc. In one embodiment, the flexible material may also be resilient by additionally exhibiting a certain amount of elasticity, and in another embodiment, the material may be flexible without any exhibiting significant elastic qualities.

The strip 5 may have a top surface 11 (FIG. 1), a bottom surface 12 (FIG. 1B), a contoured peripheral edge surface or sidewall 10 (FIG. 1A) to create a strip 5 of thickness 9. The strip 5 may have a configuration that, very broadly speaking, has a peripheral edge contour surface 10 that generally provides the strip with a very elongated triangular shape. The strip 5 may be considered to have a first end 13 and a second end 14. The first end 13 may have a concave edge portion 15 between a first convex-shaped tip 16 and a second convex-shaped tip 17, while the second end 14 may comprise a single convex-shaped tip 18. The first convex-shaped tip 16 and second convex-shaped tip 17 may each generally comprise a rounded edge surface that transitions into the elongated portion of the strip 5, as follows.

Between the first convex-shaped tip 16 at first end 13, and the convex-shaped tip 18 at second end 14, there may be a first elongated edge surface 19. The first elongated edge surface 19 may generally be formed to be concave over at least a portion of its length. A curved edge surface 20 may serve as a transition between the convex-shaped first tip 16 and the first elongated edge surface 19, and therefore, surface 20 may generally have a smaller radius of curvature than that of the second first elongated edge surface 19. Also, a curved edge surface 21 may serve as a transition between the first elongated edge surface 19 and the convex-shaped tip 18 at second end 14.

Similarly, between the second convex-shaped tip 17 at first end 13, and the convex-shaped tip 18 at second end 14, there may be a second elongated edge surface (or wall) 22. The second elongated edge surface 22 may generally be formed to be convex over at least a portion of its length. A curved edge surface 23 may serve as a transition between the convex-shaped second tip 17 and the second elongated edge surface 22. Curved transition edge surface 23 may generally be concave, and may have a varying radius of curvature to make the transition as desired. Also, a curved edge surface 24 may serve as a transition between the second elongated edge surface 22 and the convex-shaped tip 18 at second end 14.

The bottom surface 12 of the strip 5 preferably comprises two or more adhesive regions to permit temporary bonding of the strip 5 onto a person's face using pressure, as further described hereinafter, and thus may include at least one adhesive free region. The adhesive may preferably be an adhesive that is releasable, so as to permit adjustments in the placement of the strip, as described hereinafter. The strip 5 may also comprise an adhesive area in which one portion has an adhesive capability that is measurably reduced from the adhesive capability of the remaining portion, which may serve to aid in having the edges of the strip releasable for positional adjustments. However, the adhesive at the edges of the strip must nonetheless have sufficient adhesion capability so that the strip remains in place on the user's face during sleep and/or physical activity. In a preferred embodiment, the strip 5 may preferably comprise adhesive regions 25 and 26, which are shown with cross-hatching in FIG. 1B. It may also be an adhesive which provides an amount of tack which increases with the passage of time. The adhesive may also preferably be hypoallergenic, and may include, but not be limited to, a hypoallergenic single polymer acrylate adhesive, or a hydrocolloid adhesive elastomer.

The adhesive regions of the finished strip 5 may have a removable protective strip applied thereto, in order to protect the adhesive regions prior to use. The removable protective strip should be manufactured of a suitable material or comprise a material coating adapted to resist the bonding capability of the adhesive, so that it can be peeled off of the adhesive to leave the adhesive of the strip ready for application to a user's face.

Figure 1A:
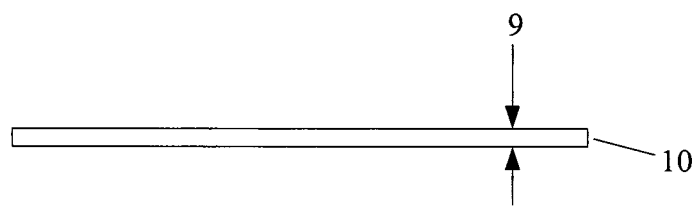
FIG. 1A is a side view of the nasal passage expander of FIG. 1.
Figure 1B:
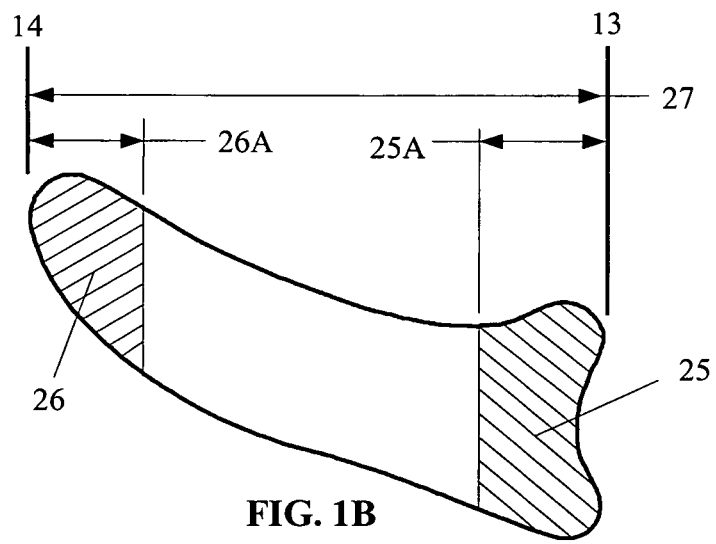
FIG. 1B is a bottom view of the nasal passage expander of FIG. 1.

As seen in FIG. 1B, the first adhesive region 25 may begin at the extreme peripheral edge of the first end 13 of strip 5, and terminate along a linear edge defined by dimension 25A. The second adhesive region 26 may begin at the extreme peripheral edge of the second end 14 of strip 5, and terminate along a linear edge defined by dimension 26A. Therefore, the strip illustrated in FIG. 1B may have a total length 27, of which only the cross-hatched portions denoted by dimensions 25A and 26A may have an adhesive covering, although, as previously stated, the entire length 27 of strip 5 may be covered in adhesive.

Figure 2:
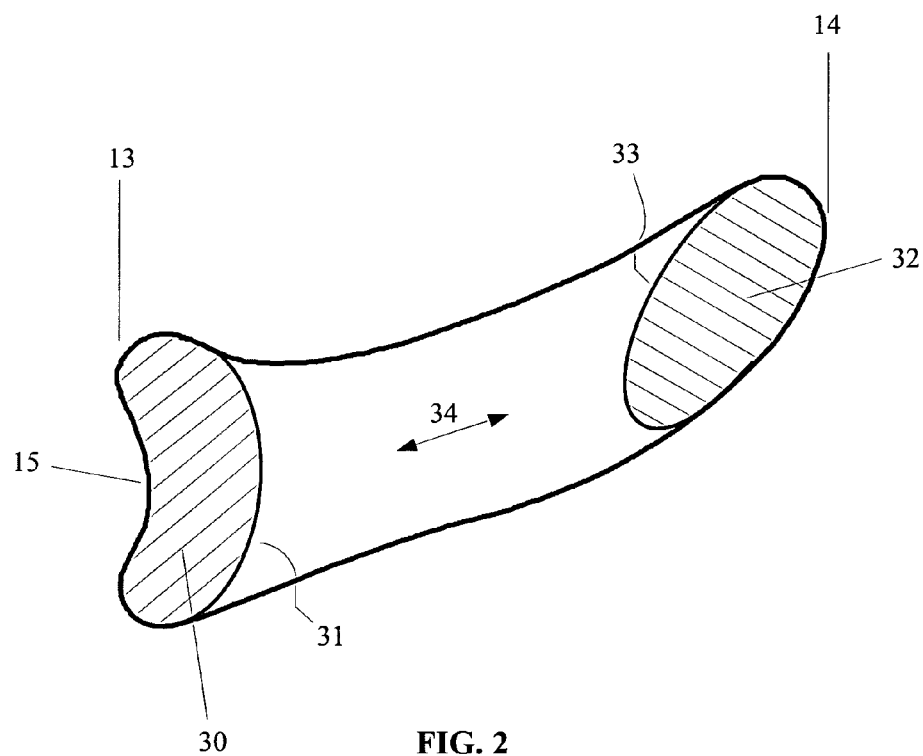
FIG. 2 is a top view of the nasal expander of the present invention.

Alternatively, as seen in FIG. 2, strip 5 may have a first adhesive region 30 beginning at first end 13 that can have any desired interior edge shape, being defined by an inner adhesive edge contour 31. The contour may, for example, be convex shaped to provide a certain minimum amount of adhesive centrally due to concave edge portion 15, and may thus generally resemble a "bean" shape or kidney shape. Similarly, there may be a second adhesive region 32 beginning at second end 14 that can also have any desired internal shape defined by inner adhesive edge contour 33. Thus, the second adhesive region 32 may be an ovoid or egg-shaped region.

The adhesive regions may be adapted to provide adequate retention of strip 5 on the face of a user, when applied properly, which may cause a certain amount of tension in the strip between first end 13 and second end 14, and which must be countered by the adhesive providing the requisite amount of shear strength and resistance to peeling from the user's face, until being deliberately removed therefrom. The region 34 between the first adhesive region 30 and the second adhesive region 32 may preferably be free of adhesive. Although region 34 may alternatively comprise an adhesive surface and thereby interconnect regions 30 and 32 into a single large adhesive region, maintaining region 34 free of adhesive better enables a wearer to more easily and properly apply the strip, as adhesive in region 34 could potentially contact a skin surface between the alar facial groove and the cheek area without sufficient tension existing between the first and second ends of the strip. It is this tension which serves to apply a lateral force to the alar facial groove to dilate the nasal passage. Therefore, in a preferred embodiment of strip 5, region 34 will be free of adhesive to better enable a user to apply the strip with the requisite amount of tension to achieve the desired amount of nasal passage dilation.

Figure 4:
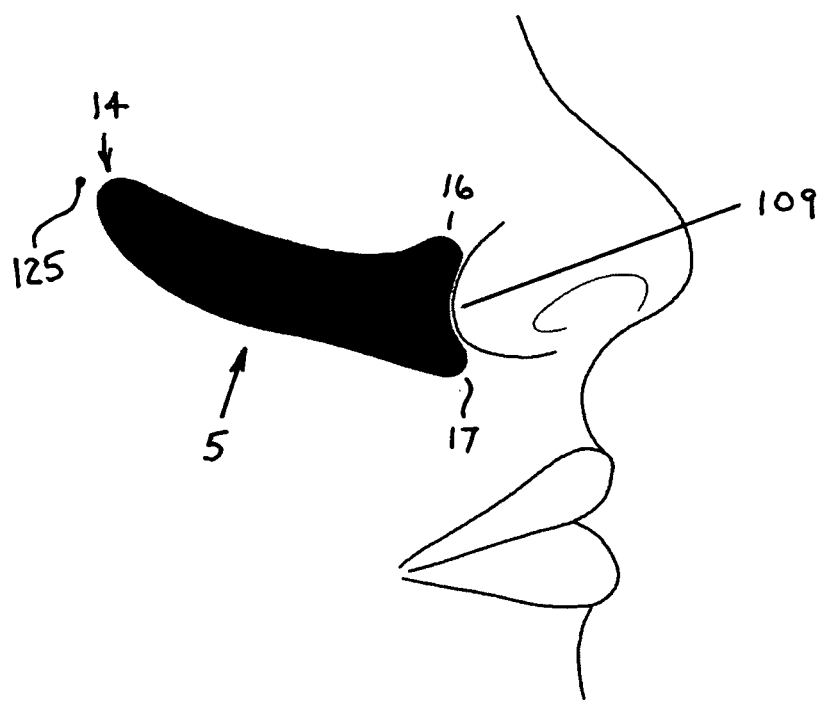
FIG. 4 shows the nasal expander of the present invention in position on a user.
Figure 8:
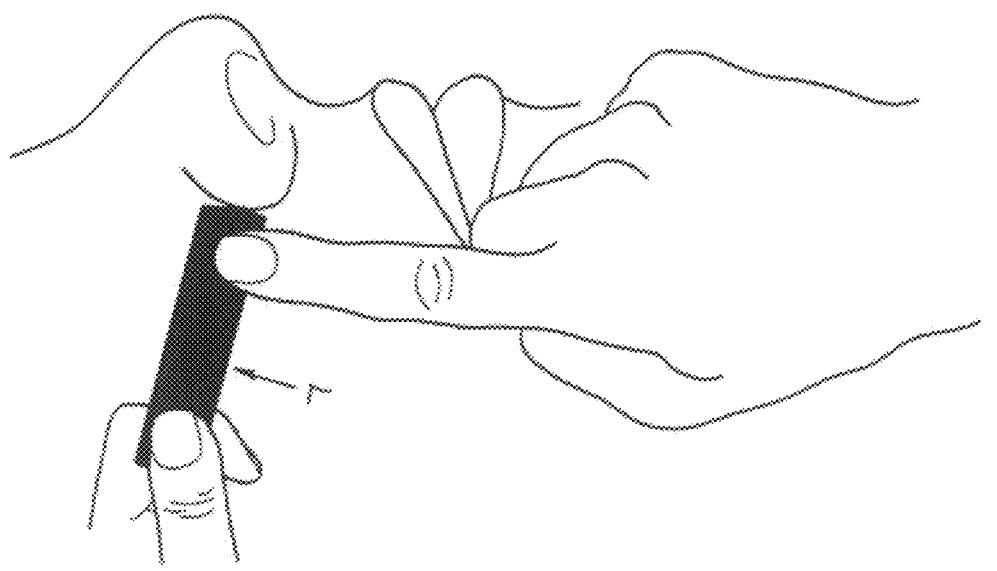
FIG. 8 shows a representative strip being applied to the alar facial groove of a user, in accordance with various embodiments.
Figure 9:
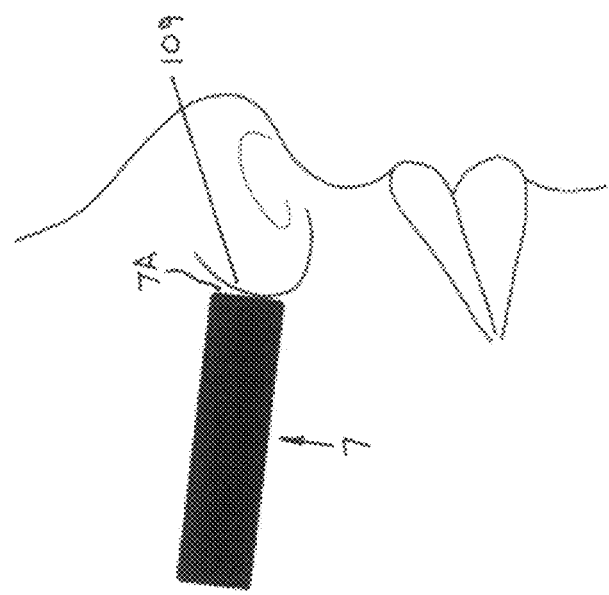
FIG. 9 shows a representative rectangular-shaped strip, in accordance with various embodiments.
Figure 10A:
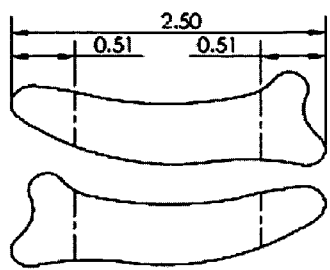
FIG. 10A shows one representative example of the size of the strip of the present invention.
Figure 10C:
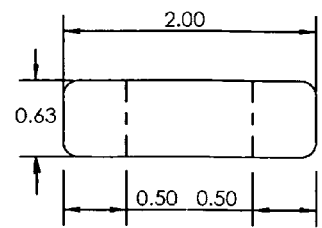
FIG. 10C show one representative example of the size of a rectangular-shaped strip of the present invention.
Figure 10B:
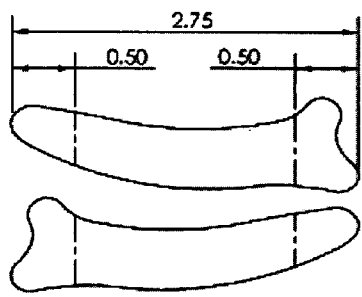
FIG. 10B shows a second representative example of the size of the strip of the present.
Figure 10D:
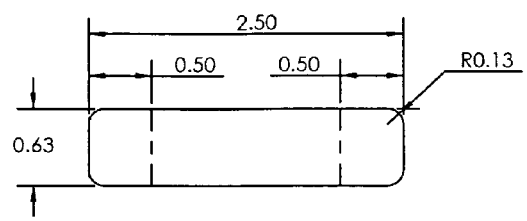
FIG. 10D show a second representative example of the size of the rectangular strip of the present invention.
Figure 11A:
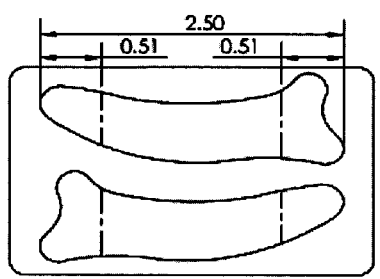
FIG. 11A shows a first sheet having a first pair of nasal passage expanders of the present invention located thereon.
Figure 11C:
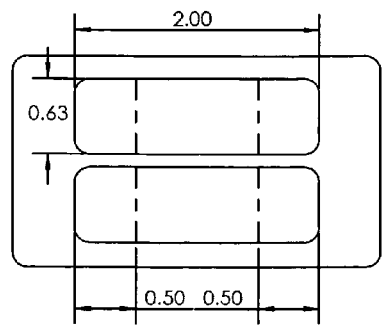
FIG. 11C show a third sheet having a first pair of rectangular-shaped nasal passage expanders of the present invention located thereon.
Figure 11B:
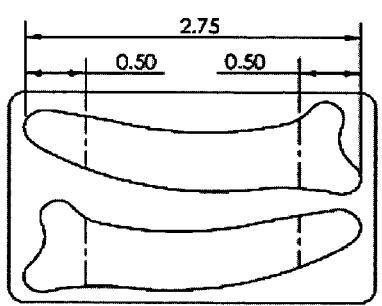
FIG. 11B shows a second sheet having a second pair of nasal passage expanders of the present invention located thereon.
Figure 11D:
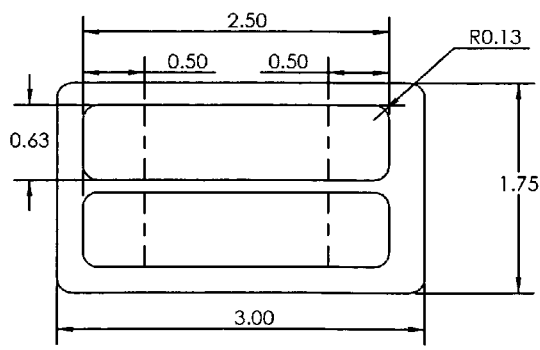
FIG. 11D shows a fourth sheet having a second pair of rectangular-shaped nasal passage expanders of the present invention located thereon.
Figure 12A:
FIG. 12A is an enlarged view of the strip of the current invention, exemplifying the use of graphics being displayed on the outward facing side.
Figure 12B:
FIG. 12B is an enlarged view of the sports version of the strip of the current invention.

It will be appreciated that while a specific configuration for the nasal passage expander of the present invention is shown in FIGS. 1 and 2 the shape of the strip and the location or shape of the adhesive regions may be tailored in a number of various way as desired, particularly as needed to suit the differently shaped and sized faces of specific users. However, one particular alternative embodiment—a strip 7—is shown being applied to the alar facial groove of a user, in FIG. 8. As seen more readily in FIG. 9, the strip 7 may be rectangular-shaped, and while it may abut the alar facial groove, the flat peripheral edge surface 7A does not lend itself to closely following the nose contour of the user nearly as well as the curved peripheral edge surfaces of first end 13 of strip 5 (FIG. 4). But a black-colored strip 7, when properly positioned, nonetheless serves to dilate a user's nasal passage, although perhaps being somewhat less effective. But, the rectangular shaped strip 7 additionally serves to resemble the grease paint, shoe polish, or adhesive backed patches that athletes apply to their faces below the eye to prevent light from reflecting off from their cheeks and into the peripheral areas of the eye.

Figure 3:
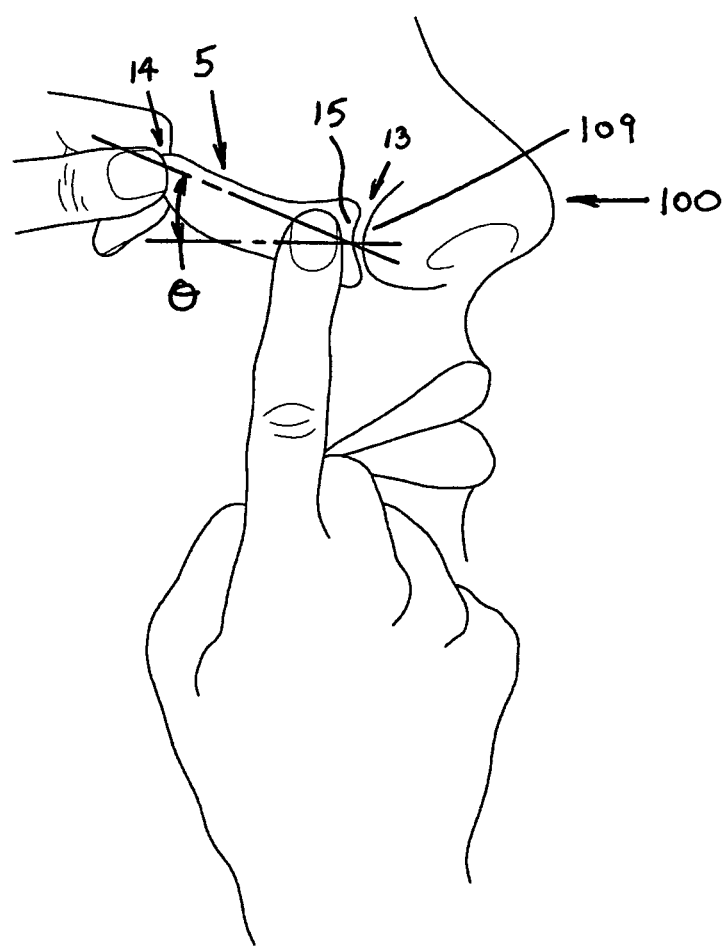
FIG. 3 is a view of the nasal passage expander of the present invention being applied to a user's face.
Figure 3A:
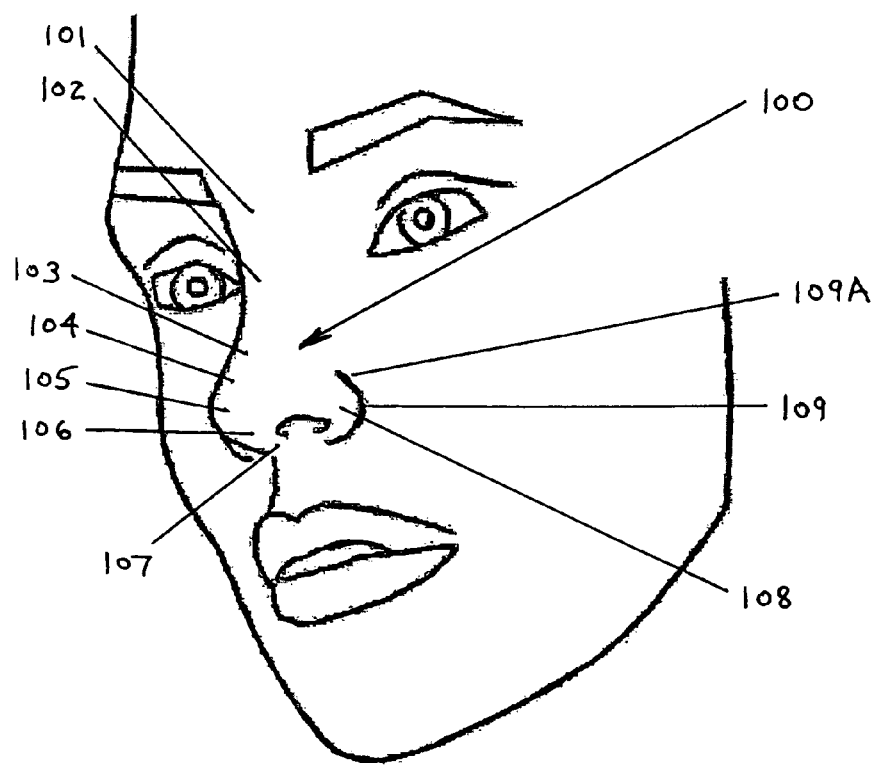
FIG. 3A is a view of a user's face, with identification thereon of anatomical features of the user's nose.

The process of applying the strip 5 first requires that the protective covering be removed from at least the first adhesive region (25 or 30) at the first end 13, so that the first end 13 of the strip may first be applied to the user's face. Removal of the protective covering from the second adhesive region (26 or 32) may preferably occur later. The first adhesive region at first end 13 may preferably be applied to the portion of the user's face adjacent to the side of the nose, at the lower end of the nose, as illustrated in FIG. 3. (The surface anatomy of a person's nose is depicted and labeled in FIG. 3A to assist in understanding both the application process and the effectiveness of the strip 5 herein) This portion of the nose, at which the first end 13 is to be applied, is referred to as the alar facial groove or junction 109, which forms an edge of the alar sidewall 108.

Generally speaking, when the nasal passage expanding strip 5 is properly positioned on a user's face (FIG. 3), the strip appears to rise from the first end 13 to the second end 14 so that the second end 14 is positioned higher on the face of a user than the first end 13. To enlarge the nasal passage according to the present disclosure, the strip 5 operates to provide a lateral displacement force to the nose at the alar facial groove. However, directly lateral to the alar facial groove, on the face of many people, is the skin below the cheek bone, where the inside of the mouth lining has not quite reached the cheek bone. This portion of skin tends to be somewhat loose, and is not ideal in providing support for the lateral displacement needed for nasal passage dilation. Conversely, the skin at a person's cheekbone tends to be more firm, and is capable of better support. So, the strip 5 is adapted to angle upward slightly, through the first elongated edge surface 19 (concave) and second elongated edge surface 22 (convex), to attach at the skin proximate to the cheek bone—a little before the center of the zygomatic bone, at its center, or slightly beyond. This attachment arrangement serves to increase lateral displacement without unnecessarily distorting the person's skin and mouth, while enabling the effective nasal dilation through the following strip application process. In a preferred embodiment of the present invention, strip 5 may comprise a strip of sufficient length to at least go over/across the cheek bone to be secured thereto. The strip may preferably be two inches or longer in length.

The shape of the first end 13 of strip 5 is crucial, because the concave edge portion 15 of strip 5 between first convex-shaped tip 16 and second convex-shaped tip 17 is deliberately contoured as shown to facilitate its placement not only in proximity to the facial groove 109 of nose 100, but to be immediately next to alar facial groove 109. The part of the triangular shape of the strip created by first convex-shaped tip 16 and second convex-shaped tip 17 serves not only to provide sufficient surface area for securing that adhesive surface to that facial region, but also to provide a portion therein with a surface area of contact at the upper portion of the alar facial groove 109A, which is achieved by the first convex-shaped tip 16, to thereby assist in opening the nasal passage.

Although the first end 13 may be clocked at various different orientations relative to the curved portion 101 of the user's nose, the clocking should generally be such that the strip 5 extends laterally across the user's face, with the second end 14 tending to be directed slightly upward and back towards the user's cheekbone, which generally comprises its ultimate placement, as seen in FIG. 3. This angle, θ, may be quite small for some individuals, possibly even being zero degrees, but in general it will be between 15-30 degrees, and may preferably be, for many individuals, approximately 20 to 25 degrees, as illustrated in FIG. 3. Since the angle tends to be relatively small, the majority of the tension in the properly applied strip 5 will be resolved to be in the lateral direction and will serve to dilate the nasal passage, while any upward component of the tension force will be much smaller, and will not reduce in any way the dilation resulting from the lateral force component.

Depending on the length of the strip 5 utilized, the second end may fall just short of reaching the cheek bone before being secured to the user's face. However, in a preferred embodiment, the strip 5 may be of sufficient length to reach and be secured to the user's face at the cheekbone of the user, or possibly may be incrementally longer to permit it to be secured at a point distal from both the nose and the cheekbone. In any case, if the first end 13 of strip 5 is not positioned correctly so as to engage the side of the nose 100, as seen in FIG. 3, final placement of the second end 14 will not be correct, which will adversely affect the nasal passage expanding capability of the strip, which will be illustrated hereinafter.

A finger may be used to apply pressure to the first end 13 of the strip 5, when it is correctly positioned, to cause the adhesive to bond to the user's skin, after which the protective covering may be removed from the second adhesive region (26 or 32). While slight pressure is applied to the first end 13 of the strip adjacent the nose, the second end 14 of strip 5 is pulled slightly upward and away from the nose to be applied to the cheek. The proper placement of the strip 5 on a user's face is shown is FIG. 4, and comprises an application in which the length of the strip 5 is such that second end 14 of the strip does not reach the cheek bone center 125. If the user determines that the strip was improperly placed and is not providing sufficient nasal passage enlargement, or if the strip was properly oriented but an insufficient amount of pull was utilized in positioning the second end which produced an inadequate amount of dilation, the user may adjust the application by repositioning the second end 14 of the strip. The user may do so by gently releasing the second end 14, relocating it, and then refastening the adhesive surface to the user.

Figure 5:
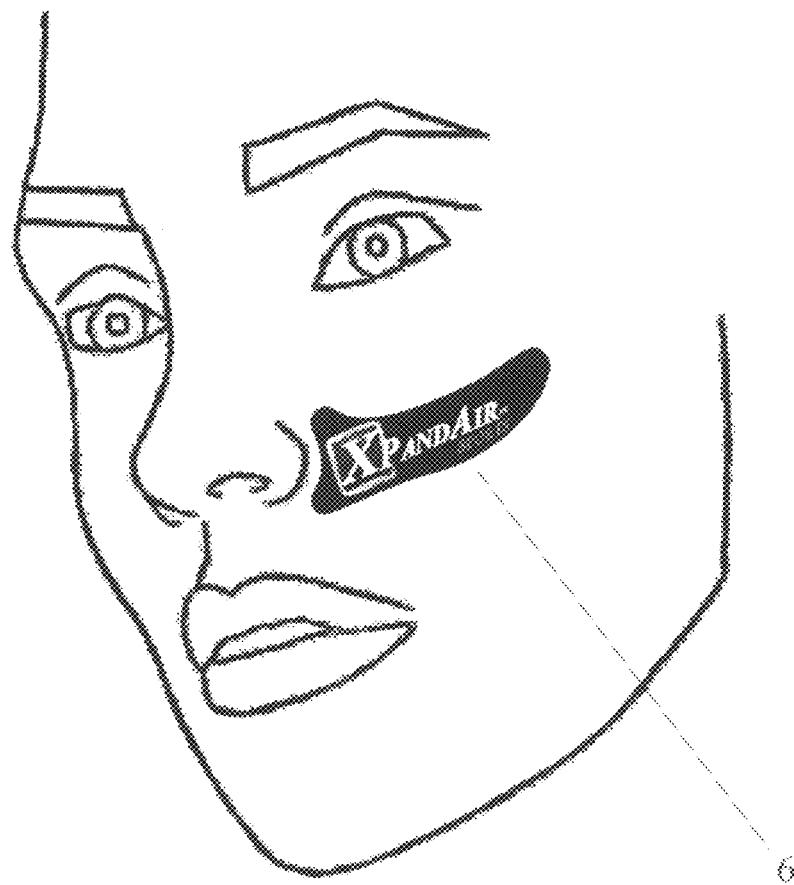
FIG. 5 is a front view of the nasal expander of the present invention on a user.

Although is possible to utilize only one strip upon a user's face—on either the left side or the right side—to accomplish nasal passage expansion on that particular side, it will likely be more common that a user will apply two strips—one on each side of his or her face. The left-hand and right-hand strip for both side of the face may be mirror image versions of the strip. The same steps may be followed in applying the corresponding strip 6 to the opposite side of the nose. FIG. 5 generally illustrates application of the strip on the opposite side of the nose. In addition, FIG. 5 also illustrates that a strip 6 may have a first side 11—the side without adhesive which may be visible to those looking at the user—which may be manufactured to have a tan colored material, or a clear see-through material, or to be an anti-reflective finish upon a black color for sports applications. The strip may also feature graphic art work to provide an aesthetically appealing visual appearance. The art work may be in the form of licensed images representing, for example, certain professional sports teams, or may instead be promotional art work for particular companies or products.

Figure 7:
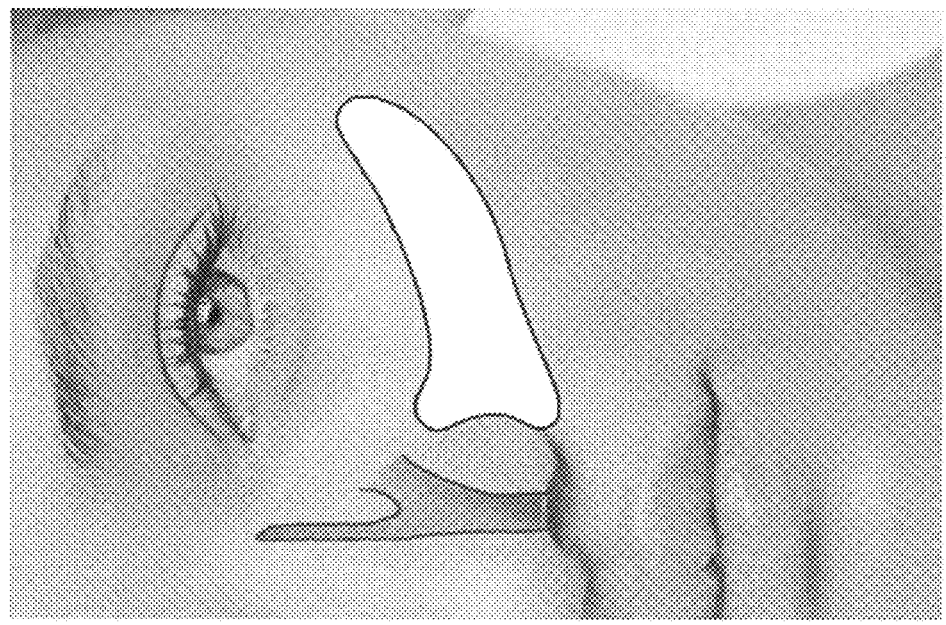
FIG. 7 shows a representation of a user's nasal passages after applying the nasal expander of the present invention.
Figure 6:
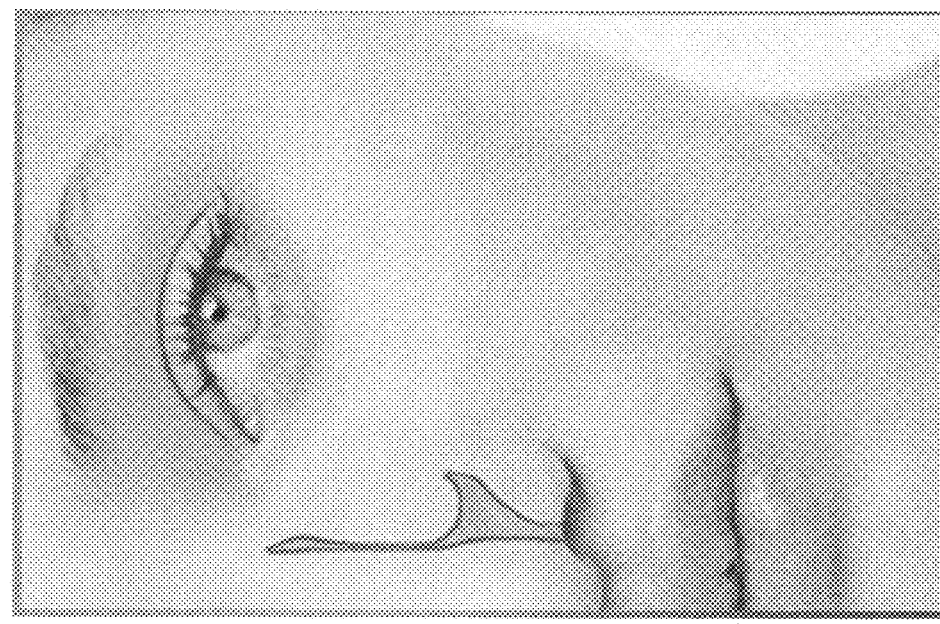
FIG. 6 shows a representation of a user's nasal passages prior to applying the expander of the present invention.

FIG. 6 shows a portion of a user's face with the nasal passages shown in an untreated condition. FIG. 7 shows the expansion of the user's nasal passages, after the strip of the present application has been applied to the user's face. As can be seen from the FIGS. 6 and 7, the strip of the present invention provides a means to open the nasal passageway and improve airflow. The strips of the present invention provide this benefit because of the combination of the size, shape, positioning and method of application of the strip. For maximum effectiveness, the first end of the strip of the present invention may preferably be adhered beyond the alar sidewall to be immediately at the alar facial groove, irregardless of the clearance shown in FIG. 5, which was shown with a gap to highlight the graphic art work.

The strips 5 and 6 of the present invention may be any suitable size. FIGS. 10A-10D show representative examples of different sized strips that can be used by a person who wants to take advantage of the benefits of this invention. Modifications to the size can be made depending on a number of factors including, but not limited to, the size of the user's face, the need to expand the passageways a greater distance, etc. FIGS. 11A-11D show a pair of sheets with first and second nasal expanders positioned thereon. In an alternate embodiment, the sheets may replace the protective covering, so that removal from the sheet exposes the adhesive on the strip.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

What is claimed is:

1. A method for expanding a nasal air passage in a nose comprising:

applying a first adhesive surface on a first end of a strip immediately adjacent to an alar facial groove of said nose of a user, wherein said first end of said strip includes a configuration having a concave edge portion between two convex portions to align with said alar facial groove;

wherein said strip has said first end, a second end, a first sidewall, a second sidewall, a top surface and a bottom surface;

wherein said first sidewall is concave over at least a portion of its surface;

wherein said second sidewall is convex over at least a portion of its surface;

wherein said second end of said strip comprises a convex-shaped tip;

at least a portion of said bottom surface at said first end of said strip comprising said first adhesive surface;

at least a portion of said bottom surface at said second end of said strip comprising a second adhesive surface;

temporarily providing pressure on said first end of said strip against said face;

pulling on said second end of said strip to stretch a portion of said face and to expand said nasal air passage, wherein said configuration of two convex portions and said concave edge portion facilitate increased expansion of said nasal passage;

applying said second end of said strip to said face while maintaining said expansion of said nasal air passage, wherein said second end of said strip is applied at an upward angle of between 15 degrees and 30 degrees, and wherein said second end of said strip is applied by bonding said second adhesive surface to said face of said user;

removing said pressure on said first end of said strip against said face, while said first adhesive maintains said first end of said strip against said face;

temporarily providing pressure on said first end of said strip against said face;

re-adjusting said second end of said strip on said face to re-increase said expansion of said nasal air passage;

re-applying said second end of said strip on said face;

wherein said second adhesive surface is releasable to allow for re-adjustment, wherein said first adhesive surface and said second adhesive surface increase tack with the passage of time;

wherein said first adhesive surface and said second adhesive surface comprise an adhesive from the group consisting of: a hypoallergenic single polymer acrylate adhesive, or a hydrocolloid adhesive elastomer; and wherein said strip comprises material sufficiently resilient to maintain said expansion of said nasal air passage, and wherein said strip material is from the group consisting of: polypropylene, polyolefin or polyesters.

2. The method according to claim 1, wherein said second end is positioned to be proximate to a cheekbone of said user.

3. The method according to claim 2, wherein said second end of said strip is positioned distally from said alar facial groove of said nose until nasal expansion occurs.

4. The method according to claim 3, wherein said second end of said strip is repositioned by gently releasing said second end, relocating said second end until said nasal expansion improves, and then refastening said second adhesive surface to said user's face.

5. The method according to claim 4, wherein one of said convex portions at said first end of said strip adheres to an upper portion of said alar facial groove.

6. A method for enlarging nasal air passages in a nose comprising:

applying a first adhesive surface on a first end of a strip immediately adjacent to an alar facial groove of said nose of a user, wherein said first end of said strip includes a crescent configuration to align with said alar facial groove;

wherein said strip has said first end a second end a first sidewall, a second sidewall, a top surface and a bottom surface;

wherein said first sidewall is concave over at least a portion of its surface;

wherein said second sidewall is convex over at least a portion of its surface;

at least a portion of said bottom surface at said first end of said strip comprising said first adhesive surface;

at least a portion of said bottom surface at said second end of said strip comprising a second adhesive surface;

temporarily providing pressure on said first end of said strip against said face;

pulling on said second end of said strip to stretch a portion of said face and to expand said nasal air passage, wherein said crescent configuration facilitates increased expansion of said nasal passage;

applying said second end of said strip to said face while maintaining said expansion of said nasal air passage, wherein said second end of said strip is secured to a side of said cheekbone opposite said nose, and wherein said second end of said strip is applied by bonding said second adhesive surface to said face of said user;

removing said pressure on said first end of said strip against said face, while said first adhesive surface maintains said first end of said strip against said face;

temporarily providing pressure on said first end of said strip against said face;

re-adjusting said second end of said strip on said face to re-increase said expansion of said nasal air passage;

re-applying said second end of said strip on said face while maintaining said re-increase of said expansion of said nasal air passage;

wherein said second adhesive surface is releasable to allow for re-adjustment;

wherein said first adhesive surface and said second adhesive surface increase tack with the passage of time;

wherein said first adhesive surface and said second adhesive surface comprise an adhesive from the group consisting of: a hypoallergenic single polymer acrylate adhesive, or a hydrocolloid adhesive elastomer; and wherein said strip comprises material sufficiently resilient to maintain said expansion of said nasal air passage, and wherein said strip material is from the group consisting of: polypropylene, polyolefin or polyesters.

* * * * *